(12) United States Patent
Mad Arif et al.

(10) Patent No.: US 7,329,512 B2
(45) Date of Patent: Feb. 12, 2008

(54) ALLERGENIC LATEX PROTEIN

(75) Inventors: Siti Arija Mad Arif, Sungai Buloh (MY); Nyu Ping Chew, Sungai Buloh (MY); Hoong Yeet Yeang, Sungai Buloh (MY)

(73) Assignee: Malaysian Rubber Board, Kuala Lumpur (MY)

( * ) Notice: Subject to any disclaimer, the term of this patent is extended or adjusted under 35 U.S.C. 154(b) by 481 days.

(21) Appl. No.: 10/789,312

(22) Filed: Feb. 27, 2004

(65) Prior Publication Data

US 2004/0171812 A1 Sep. 2, 2004

(30) Foreign Application Priority Data

Feb. 28, 2003 (MY) .............................. PI 20030734

(51) Int. Cl.
- *C07H 21/04* (2006.01)
- *C12N 15/09* (2006.01)
- *C12N 15/00* (2006.01)
- *C12N 1/20* (2006.01)
- *C12N 5/02* (2006.01)

(52) U.S. Cl. ..................... 435/69.3; 435/455; 435/325; 435/252.3; 435/320.1; 536/23.1

(58) Field of Classification Search ..................... None
See application file for complete search history.

(56) References Cited

OTHER PUBLICATIONS

Attwood et al. The Babel of Bioinformatics. Science 290:471-473.*
Skolnik et al. 'From genes to protein structure and fucntion: novel applications of computational approaches in the genomic era.' Trends in Biotech 18:34-39, 2000.*
Villalba et al. 'Cloning and Expression of Ole e I, the major allergen from Olive Tree Pollen.' J. Biol. Chem. 269(21): 15217-15222, 1994.*
Arif et al. Isolation and charaterization of the early nodule-specific protein homologue (Hev b 13), an allergenic lipolytic esterase from *Hevea brasilienses* latex. J. Biol. Chem. 23:23933-23941, 2004.*
Lazar et al. 'Transforming Growth Factor alpha: Mutation of Aspartic Acid 47 and Leucine 48 Results in Different Biological Activities.' Molec. Cell. Biol. 8(3):1247-1252.*
Bowie et al. 'Deciphering the Message in Protein Sequences: Tolerance to Amino Acid Substitutions.' Science 247:1306-1310.*
Wang et al. 'A Single Amino Acid Determines Lysophospholipid Specificity of the S1P, (EDG1) and LPA, (EDG2) Phospholipid Growth Factor Receptors.' J. Biol. Chem. 52(28):49213-49220, 2001.*
Burgess et al. 'Possible dissociation of the Heparin-binding and Mitogenic Activities of Heparin-binding (Acidic Fibroblast) Growth Factor-1 from Its Receptor-binding Activities by Site-directed Mutagenesis of a Single Lysine Residue.' J. Cell. Biol. 111:2129-2138, 1990.*
"Identification of Latex Protein Allergens", D.H. Beezhold, et al., Paper presented at 'International Conference on Latex Protein Allergy: The Latest Poition', Jan. 11, 1995, pp. 19-27.
cDNA cloning of the 43-kDa latex allergen Hev b 7 with sequence similarity to patatins and its expression in the yeast *Pichia pastoris*, S. Sowka, et al., Eur. J. Biochem., vol. 255, 1998, pp. 213-219.
"Cloning and characterization of a latex allergen (*Hev b 7*): homology to a patatin, a plant $PLA_2$", D.A. Kostyal, et al., Clin. Exp. Immunol., vol. 112, 1998, pp. 355-362.
"Allergenic proteins of natural rubber latex", H.Y. Yeang, et al., Methods, vol. 27, 2002, pp. 32-45.

* cited by examiner

*Primary Examiner*—Maher M. Haddad
*Assistant Examiner*—Nora M. Rooney
(74) *Attorney, Agent, or Firm*—Weingarten, Schurgin, Gagnebin & Lebovici LLP

(57) ABSTRACT

The present invention relates to a protein found in natural rubber that can induce an allergic reaction in persons who have been sensitised to it. The invention provides for the process of isolating and purifying the protein and describes the characteristics of the protein, including its molecular weight, isoelectric point, amino acid sequence and allergenicity. The invention also describes the isolation and cloning a the DNA that encodes the protein. The production of the recombinant version of the protein using a protein expression vector is described.

11 Claims, 7 Drawing Sheets

Fig. 1A

```
DNA:  acgcgggggcgttaacacttggttttttgcttccacttcatggagttccctg        51
      ----1----1----1----1----1----1----1----1----1----1-

DNA:  aaaccaataacaaccctatcatcactctctcttctttcttattatgcatgcttt        102
      ---1----1----1----1----1----1----1----1----1----1--

DNA:  ccctagcttatgcttccgaaacctgtgattttccagcaatctttaacttcg          153
      --1----1----1----1----1----1----1----1----1----1---

DNA:  gcgactccaattccgataccggtggcaaggcagctgccttttatcctctta          204
      -1----1----1----1----1----1----1----1----1----1----

DNA:  accctccttatggagagactttctttcacaggtcgacaggaaggtactctg          255
      1----1----1----1----1----1----1----1----1----1----1

DNA:  atggaaggctcataatagatttttatcgccgagagtttcaatctcccatatc         306
      ----1----1----1----1----1----1----1----1----1----1-

DNA:  tgagtccatatcttagttccctgggaagcaacttcaaacatggtgcagatt          357
      ---1----1----1----1----1----1----1----1----1----1--

DNA:  ttgccacagcaggatccaccattaaactaccaactactattatacctgctc          408
      --1----1----1----1----1----1----1----1----1----1---

DNA:  atggtggatttagtccattctaccttgatgtccaatattcgcaattccggc          459
      -1----1----1----1----1----1----1----1----1----1----

DNA:  aattcatacccagatcacagtttatcagggaaactggaggcatatttgctg          510
      1----1----1----1----1----1---1----1----1----1----1

DNA:  aattggtgcccgaggaatattattttgagaaagctttatacacattcgata          561
      ----1----1----1----1----1----1----1----1----1----1-

DNA:  ttggtcaaaatgatcttacagaaggattcttgaacttaactgtggaagaag          612
      ---1----1----1----1----1----1----1----1----1----1--

DNA:  tgaatgcaactgtccctgatcttgtgaatagcttctcagcaaacgttaaga          663
      --1----1----1----1----1----1----1----1----1----1---

DNA:  aaatatacgatttgggagctagaacattttggattcacaacacaggaccaa          714
      -1----1----1----1----1----1----1----1----1----1----

DNA:  ttggttgtctttcattcattttaacgtattttccctgggcagaaaaggata          765
      1----1----1----1----1----1----1----1----1----1----1

DNA:  gtgcaggctgtgcaaaagcttacaatgaagttgctcagcattttaatcaca          816
      ----1----1----1----1----1----1----1----1----1----1-

DNA:  agttgaaggagatcgttgctcaactcaggaaggatttgcctttagctacat          867
```

```
             ---1----1----1----1----1----1----1----1----1----1--
DNA: tcgtccacgttgacatctattctgtcaagtattctttattcagtgagccag          918
        --1----1----1----1----1----1----1----1----1----1---

DNA: aaaaacacggtttcgagtttccacttataacatgttgtggctacggaggaa           969
       -1----1----1----1----1----1----1----1----1----1----

DNA: agtacaattttagtgttactgctccatgtggagatacagttacagcagacg          1020
      1----1----1----1----1----1----1----1----1----1----1

DNA: acggtaccaaaatagttgtgggttcatgtgcttgcccttcagttcgagtaa          1071
     ----1----1----1----1----1----1----1----1----1----1-

DNA: attgggatggagctcactacactgaagctgccaatgaatattttttcgacc         1122
        ---1----1----1----1----1----1----1----1----1----1--

DNA: agatttctacaggagccttctctgatcccctgttccattgaatatggcat          1173
       --1----1----1----1----1----1----1----1----1----1---

DNA: gtcataaaactgaatcattgaggacattagcctctgtataggttatatgaa          1224
      -1----1----1----1----1----1----1----1----1----1----

DNA: agtgctttgctgaaagcccgctaataaaatgaggaataataataaatgaga          1275
     1----1----1----1----1----1----1----1----1----1----1

DNA: aaccattgattatgttaggattcacttggtttctatcataataatctatct          1326
     ----1----1----1----1----1----1----1----1----1----1-

DNA: gttgtatatacaacagttgtatgaaatagtttcttgtaataaagacttgtc          1377
       ---1----1----1----1----1----1----1----1----1----1--

DNA: tttctccggtttcccta       1394
        --1----1----1----
```

Fig. 1B

```
AGALTLGFCFHFMEFPETNNNPIITLSFLLCMLSLAYASETCDFPAIFNF
----1----1----1----1----1----1----1----1----1----1    50

GDSNSDTGGKAAAFYPLNPPYGETFFHRSTGRYSDGRLIIDFIAESFNLP
----1----1----1----1----1----1----1----1----1----1    100

YLSPYLSSLGSNFKHGADFATAGSTIKLPTTIIPAHGGFSPFYLDVQYSQ
----1----1----1----1----1----1----1----1----1----1    150

FRQFIPRSQFIRETGGIFAELVPEEYYFEKALYTFDIGQNDLTEGFLNLT
----1----1----1----1----1----1----1----1----1----1    200

VEEVNATVPDLVNSFSANVKKIYDLGARTFWIHNTGPIGCLSFILTYFPW
----1----1----1----1----1----1----1----1----1----1    250

AEKDSAGCAKAYNEVAQHFNHKLKEIVAQLRKDLPLATFVHVDIYSVKYS
----1----1----1----1----1----1----1----1----1----1    300

LFSEPEKHGFEFPLITCCGYGGKYNFSVTAPCGDTVTADDGTKIVVGSCA
----1----1----1----1----1----1----1----1----1----1    350

CPSVRVNWDGAHYTEAANEYFFDQISTGAFSDPPVPLNMACHKTESLRTL
----1----1----1----1----1----1----1----1----1----1    400

ASV*VI*KCFAESPLIK*GIIINEKPLIMLGFTWFLS**SICCIYNSCMK
----1----1----1----1----1----1----1----1----1----1    450

*FLVIKTCLSPVSL
----1----1----    464
```

Fig. 2

ALLERGENIC LATEX PROTEIN

TECHNICAL FIELD OF THE INVENTION

The present invention relates in general to a protein.

BACKGROUND OF THE INVENTION

By the late 1980s and into the 90s, reports began to be received with increasing frequency in Europe and America of allergic reactions occurring among users of surgical and examination gloves made of latex and among spina bifida patients. The significant increase in the number of reports of latex allergy in the last decade has also been attributed to increased usage of latex gloves in healthcare in tandem with the rising cases of AIDS. Sensitisation to latex among healthcare workers is clearly work-related, the main cause being latex gloves, or specifically, the allergenic protein in latex gloves. Nevertheless, numerous cross-sensitivities between latex protein allergens and various food and pollen allergens are known. It is therefore not improbable that many latex-allergic patients may have been initially sensitised not only by proteins from latex products, but also by proteins from other sources.

There are hundreds of proteins found in natural rubber latex. Of these, only a small handful is allergenic (able to induce allergy). There has been much interest in identifying the proteins in Hevea latex responsible for latex allergy and considerable effort is expended on isolating and purifying the allergenic proteins from Hevea latex or latex products. Other than from the academic standpoint, elucidation of the major allergens in latex would enable antibodies to be developed against these proteins. Availability of the antibodies would facilitate the development of latex immunoassays, both for laboratory and commercial use. There are two main types of latex immunoassays 1. Immunoassays for Latex Allergy Diagnosis These diagnostics are used to determine if someone is allergic or sensitized to latex. The assays can either be of the in vitro format (usually a serological test) or of the in vivo format (skin prick tests). These assays are used in research and in healthcare.

2. Immunoassays for the Quantitation of Latex Allergens in Manufactured Products These quantitative assays determine the amount of allergenic proteins present in latex products. They are used for testing latex products such as latex gloves to determine the content of extractable latex allergens. Such immunoassays would be very valuable in latex product manufacture, particularly in the aspects of standardisation and quality control and quality assurance. The prospective customers for such immunoassays would be latex product manufacturers and regulatory agencies charged with the responsibility of ensuring product specification compliance.

Identification of the major latex allergens serves another useful function in healthcare. Purified latex allergens can be used in immunotherapy to de-sensitise latex allergic patients. When successfully undertaken, the patient no longer develops an allergic reaction to latex. This is especially important where the patient works in an environment (e.g. in healthcare) where latex products are ubiquitous.

Today, the International Union of Immunological Societies (IUIS) recognises ten latex allergens, Hev b 1 to Hev b 10. (There are other latex proteins under consideration by the IUIS.) Although there is effort being made to look for significant latex protein allergens, many researchers believe that most of the major latex protein allergens have been accounted for.

In 1995, Dr Donald Beezhold in his paper presented at *Int Conf on Latex Protein Allergy: The Latest Position* announced a new latex allergen that had partial protein homology to patatin, the major storage protein of potatoes. This 43 kDa protein is later assigned the WHO/IUIS name Hev b 7. When a recombinant version of Hev b 7 became available, it is found to be reactive with IgE from latex allergic patients. However, the proportion of patients that are sensitised to recombinant Hev b 7 is much lower than expected. Western blots that showed an active protein band around 43 kDa protein is much more commonly encountered than could be explained by IgE binding to Hev b 7. Hence, the recombinant Hev b 7 could not account for the very frequent occurrence of latex sensitivity to a protein of about 43 kDa. It is, therefore, possible that another unknown latex allergen of around 43 kDa existed. The search for this new and unknown protein has culminated in the present invention. This protein is allergenic in nature in that contact with allergenic latex protein (ALP) can induce an allergic reaction in persons sensitized to this protein.

SUMMARY OF THE INVENTION

According to the most general aspect of the present invention, there is provided a protein originating from latex that can induce an allergic reaction in persons sensitized to the protein.

Preferably, the protein or its molecular variant characterized in that the protein has the following properties:

a) has a molecular weight of about 42,000 Dalton;

b) has an isoelectric point of about 4.7;

c) binds with IgE of patients sensitized to the protein; and d) contains the amino acid sequence as in FIG. 2 or minor variations of these amino acid sequence that do not result in the allergenic properties of the protein being substantially altered.

The second aspect of the present invention provides for a process for obtaining a protein or its molecular variant where the process comprises the following steps:

a) centrifuging the latex for obtaining the bottom fraction;

b) freeze-thawing the bottom fraction for obtaining the latex B-serum; and c) isolating and purifying the protein from the B-serum obtained in (b).

The third aspect of the present invention provides for a peptide that is derived from the protein where the peptide has similar allergenic properties as the protein.

Further, the present invention provides for a DNA sequence encoding the protein or a portion of the protein where the DNA sequence (SEQ ID NO:1) is as in FIG. 1 or minor variations of this sequence.

Also, the present invention provides a method for the production of a protein or its molecular variants in recombinant form by inserting the DNA encoding the protein or a variant of the protein into an appropriate vector and inducing the vector to express recombinant protein or in recombinant form of the said variant of the protein, whereby in this case, the amino acid sequence (SEQ ID NO:5) of the above translated DNA sequence is as in FIG. 2.

BRIEF DESCRIPTION OF THE FIGURES

FIG. 1 shows the DNA sequence of the full length cDNA clone encoding the ALP.

FIG. 2 shows the amino acid sequence of the ALP derived from the translation of the cDNA clone encoding the ALP.

DETAILED DESCRIPTION OF THE INVENTION

The present invention relates to a protein isolated from the B-serum of centrifuged latex obtained by tapping the rubber tree, *Hevea brasiliensis*. The following description details how the protein can be isolated, purified and characterized, and how it might be used in cloning the cDNA encoding the protein, how recombinant versions of the protein can be obtained, how antibodies might be developed from the protein and how the protein can be used in immunoassay and immunotherapy.

EXAMPLE 1

Protein Isolation and Purification

Fresh latex from *Hevea brasiliensis* trees (clone RRIM 600) is collected into chilled containers. The latex is centrifuged at 19,000 r.p.m. (43,000 g) on a Sorvall RC 5C high-speed centrifuge for 1 h at 4-7° C. to separate it into three main fractions: the top fraction which is the rubber cream, the heavy bottom fraction and the C-serum located in between. Latex B-serum is prepared based on the method of Hsia (1958) *Trans Instn Rubb Ind*. The latex bottom fraction from centrifuged latex is washed by re-suspension in 0.4M mannitol and recovered by centrifugation. The washed bottom fraction is then subjected to repeated freezing and thawing to rupture the lutoids that are its main constituents. The lutoidic fluid, the B-serum, is recovered as the supernatant after re-centrifugation.

Figure 4:
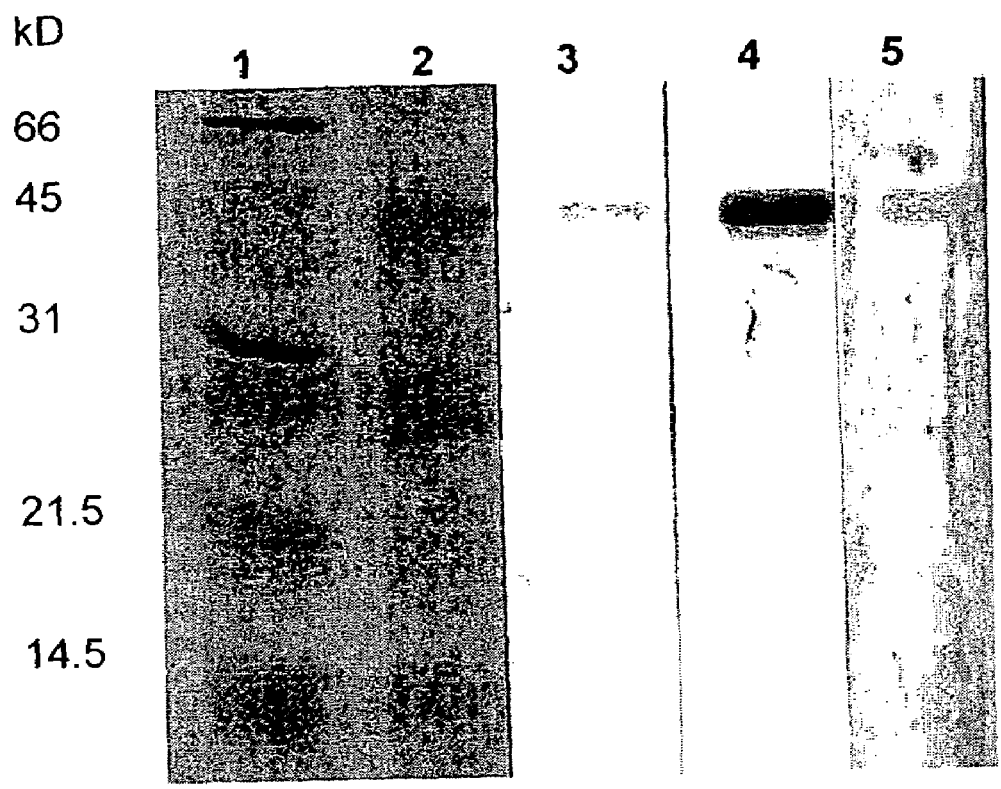
FIG. 4 shows a Western blot of ALP after separation of the protein by SDS-polyacrylamide gel electrophoresis. The protein is stained with Coomassie Blue to show the presence and electrophoretic migration of ALP (lane 2). Binding of human IgE of patients sensitised to ALP on the Western blot (lane 3), polyclonal antibodies developed against ALP (lane 4), and a monoclonal antibody developed against ALP (lane 5).

B-serum is dialysed overnight against 0.3 mM sodium borate and 0.016 M boric acid pH 7 in the cold room. This is followed with filtration through Whatman No. 1 filter paper. Ten ml of the filtered B-serum is loaded onto carboxymethyl cellulose CM32 (Whatman) column (20 cm×1.5 cm) equilibrated with 0.09 M sodium borate and 0.016 M boric acid, pH 8.6. Proteins are eluted with a gradient of 150 ml of 0.09M sodium borate and 0.016 M boric acid, pH 8.6 against 150 ml of 0.9M sodium borate and 0.16 M boric acid, pH 8.6. Two ml fractions are collected at a rate of 2.6 min/fraction. The unretarded materials (i.e. fractions 3 to 11) are loaded into a DE 52 (Whatman) column (12 cm×1.5 cm) equilibrated with 0.1 M Tris-HCl, pH 8. The protein is eluted with a gradient of 0-0.5 M NaCl in the same buffer. Fractions containing proteins of about 43 kDa, as determined by SDS-polyacrylamide gel electrophoresis, are tested for immunoglobulin IgE binding with serum latex-allergic patients. The fractions containing ALP are identified and pooled. The approximate molecular weight of ALP determined by comparing the migration of ALP with that of various calibration markers is 42 kDa (FIG. 4 lane 2).

EXAMPLE 2

Molecular Weight and Isoelectric Point Determination and Amino Acid Sequencing

Figure 3:
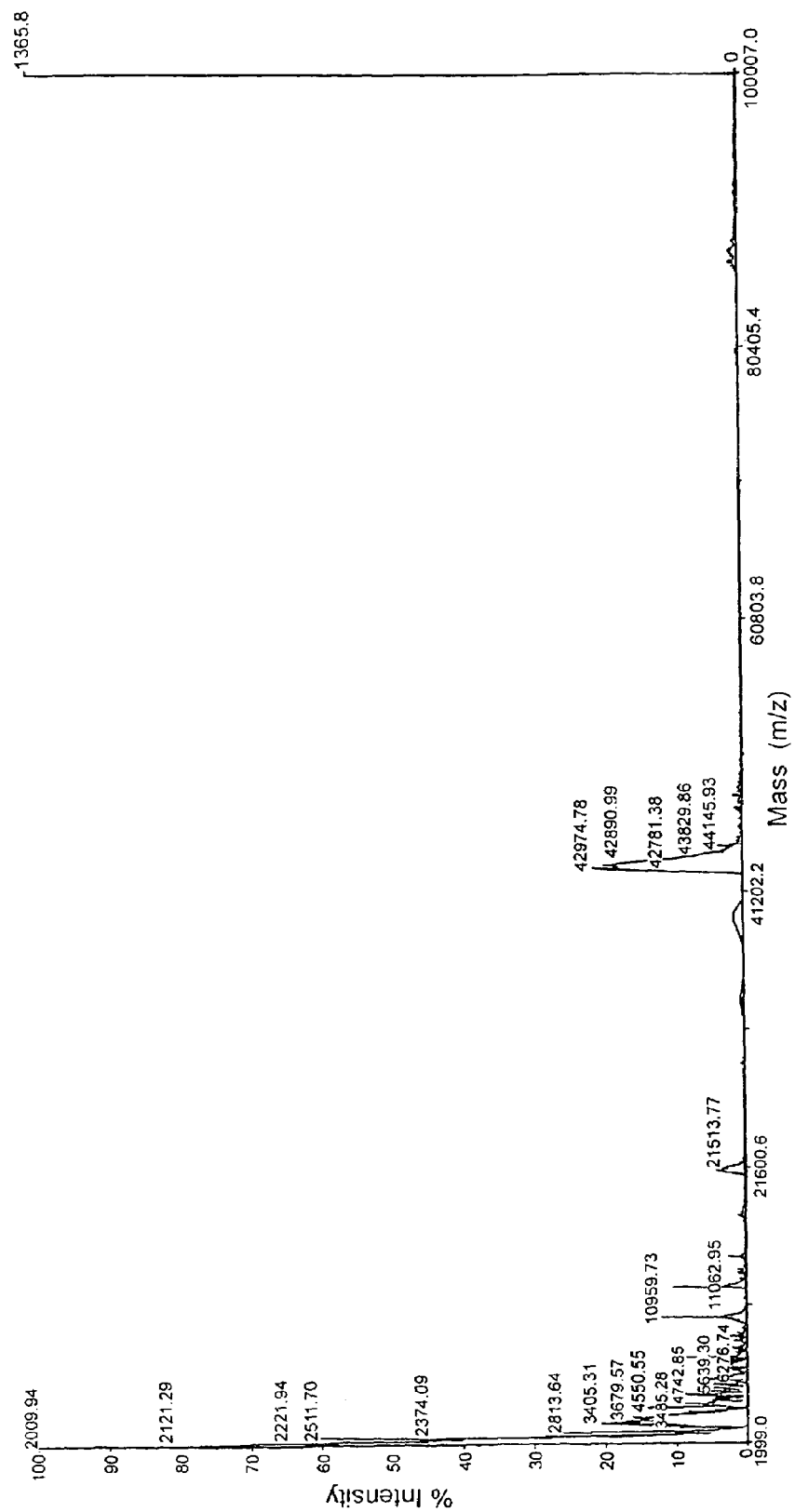
FIG. 3 shows the matrix assisted laser desorption ionisation mass spectrometry (MALDI-MS) spectrum of the allergenic latex protein, ALP.

The accurate molecular weight of the allergenic latex protein, ALP, determined by mass spectrometry is 42975. The matrix assisted laser desorption ionisation mass spectrometry (MALDI-MS) spectrum of the protein sample is shown in FIG. 3.

The isoelectric point (pI) of ALP is determined by isoelectric focusing (IEF). The migration of the protein on the IEF gel is measured and compared with protein calibration standards of known pI. The pI of ALP is estimated to be 4.7.

The protein is found to be blocked at the N-terminal. In situ digestion by trypsin resulted in several fragments. Partial amino acid sequences are obtained for three of these fragments. Sequence 1: YLDVQYSQFR (SEQ ID NO:7) Sequence 2: YSLFSEPEK (SEQ ID NO:8) Sequence 3: LPTTIIPAHGGFSSR (SEQ ID NO:6) where the letters of the alphabet are accepted abbreviations for individual amino acids.

Sequence 1 is derived from a peptide of 1319 Da. The amino acid sequence data obtained by mass spectrometry is compared against the protein sequence database of the National Centre for Biotechnology Information (NCBI), USA, using the BLAST algorithm. The search revealed that the amino acid sequences had partial homology with the "early nodule-specific protein" of *Glycine max*.

Sequence 2 is derived from a peptide of 1100 Da. The sequence showed partial homology with "early nodule-specific protein" of *Medicago truncatula*.

Sequence 3 is derived from a peptide of 1556 Da. The sequence showed partial homology with "early nodule-specific protein" of *Glycine max*.

EXAMPLE 3

Determination of Glycosylation of ALP

Figure 5:
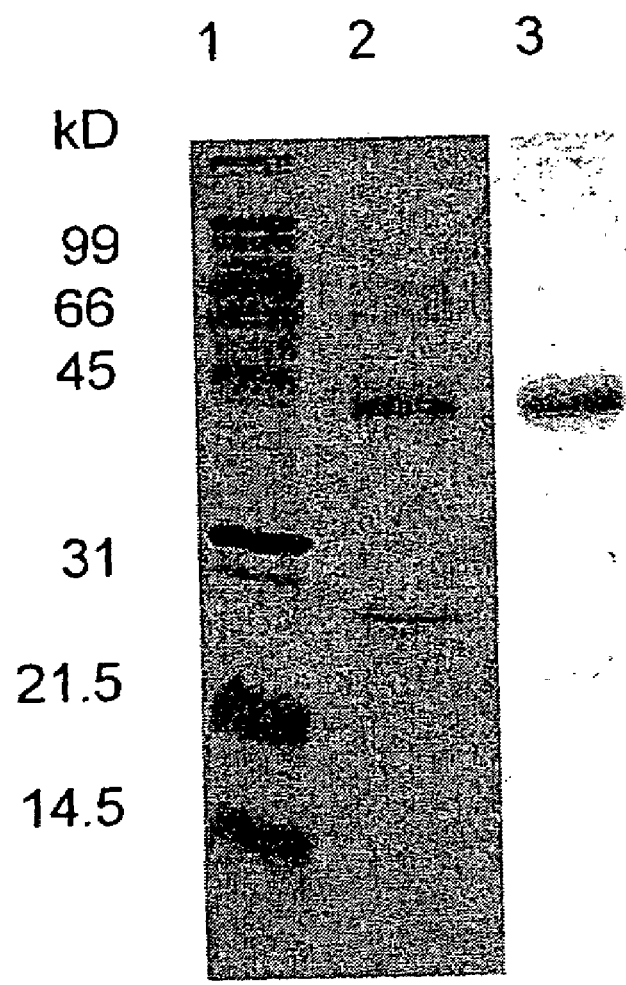
FIG. 5 shows a Western blot of ALP after separation of the protein by SDS-polyacrylamide gel electrophoresis. The protein is stained with Coomassie Blue to show the presence and electrophoretic migration of ALP (lane 2). A reaction specific for the presence of carbohydrates is carried out to demonstrate glycosylation of ALP (lane 3).

To demonstrate that a carbohydrate is bound to the ALP protein (rendering ALP a 'glycosylated protein' or glycoprotein), purified proteins are separated by SDS-polyacrylamide gel electrophoresis (SDS-PAGE) on 15% gels and transferred electrophoretically to a nitrocellulose membrane to obtain a Western Blot. The membrane is washed with phosphate buffered saline (PBS) and then immersed into 10 mM sodium periodate/EDTA with agitation in the dark for 20 min. Following this, the membrane is washed three times with PBS for 10 minutes each cycle. The membrane is next transferred to a solution made up of biotin-hydrazide in sodium acetate/EDTA and agitation is carried out for 60 min. After washing three cycles with Tris-buffered saline (TBS), the membrane is blocked and then washed over another three cycles with TBS. The membrane is then immersed in strepavidin-alkaline phosphatase for 60 min. After another three cycles of washing with TBS, the membrane is immersed in a solution of 5-bromo-4-chloro-3-indolyl phosphate/nitro blue tetrazolium (BCIP/NBT) substrate. The appearance of the coloured alkaline phosphatase reaction product indicated the presence of the carbohydrate component of the glycoprotein (FIG. 5).

EXAMPLE 4

Production of Antibodies Against ALP

Both polyclonal antibodies and monoclonal antibodies are successfully developed against ALP.

Polyclonal Antibodies Against ALP

A pure preparation of ALP (approximately 0.5 ml of 0.5 mg ALP/ml) in phosphate buffered saline (PBS) is mixed with an equal volume of complete Freunds' adjuvant and this antigen mixture is injected subcutaneously into the back of rabbits. Seven booster dose of the same antigen formulation, but with incomplete Freunds' adjuvant, are administered at two week intervals. Blood is drawn from the rabbits to obtain the anti-serum that contained polyclonal antibodies against ALP.

To demonstrate polyclonal antibody binding to ALP, a Western blot of the protein on to nitrocellulose membrane is prepared as in Example 3. The nitrocellulose membrane is blocked with 5% non-fat milk in PBS and then incubated for 90 min with anti-ALP polyclonal antibodies (diluted 1:800 in PBS-milk) as the primary antibody. After three cycles of washing with PBS-milk, the nitrocellulose membrane is incubated for 1 h with the secondary antibody, anti-rabbit IgG conjugated to alkaline phosphatase. After a further three cycles of washing with PBS-milk, the nitrocellulose membrane is incubated for 10 min in Tris buffered saline (TBS) before being immersed in 5-bromo-4-chloro-3-indolyl phosphate/nitro blue tetrazolium (BCIP/NBT) substrate to generate the coloured alkaline phosphatase reaction product. The binding of polyclonal antibodies to ALP on a Western blot of the protein after separation of the protein by SDS-polyacrylamide gel electrophoresis is shown in FIG. 5 (lane 4).

Monoclonal Antibodies Against ALP

Spleen cells from a Balb/c mouse immunized with latex C-serum are fused with mouse myeloma cells following protocols previously described by Kohler and Milstein (12, 13). The resulting hybridoma cells are screened for antibodies specific to C-serum proteins. Selected hybridomas are re-cloned twice and monoclonal antibodies secreted are used either in unpurified form in hybridoma cell supernatants or as preparations purified by affinity chromatography.

To demonstrate monoclonal antibody binding to ALP, a Western blot of the protein on to nitrocellulose membrane and processed as for the polyclonal antibody, except that monoclonal antibody against ALP is used as the primary antibody, while anti-mouse IgG conjugated to alkaline phosphatase is used as the secondary antibody. The binding of monoclonal antibodies to ALP on a Western blot of the protein after separation of the protein by SDS-polyacrylamide gel electrophoresis is shown in FIG. 4 (lane 5).

Recombinant Monoclonal Antibodies Against ALP

An anticipated variation of the conventional monoclonal antibody is the recombinant antibody whereby the antibody can be generated using a specific segment of DNA that encodes the amino acid sequence of the antibody or a functional fragment of the antibody such as a single chain variable fragment. There are several approaches to the development of recombinant antibodies, of which an example is outlined here. Antibody gene libraries are first constructed, for example, by PCR-amplification from B-lymphocyte cDNA. To screen these libraries, antibodies are displayed on the surface of microorganisms containing the antibody's gene (phage display). They are challenged with the antigen protein to identify specific clones producing an antibody that bind to this protein. Once the organism bearing the antibody gene is identified, specific clones can then be amplified and used to produce the antibody fragment in *E. coli* or other suitable organism.

EXAMPLE 5

Demonstration of Protein Allergenicity

A Western blot of the purified protein is incubated with blood serum from latex allergic patients to determine if IgE (the immunoglobulin that mediates the allergic reaction) bound to the protein. Binding of IgE to the protein indicated that the protein is allergenic.

To detect protein-IgE binding in Western blots, a similar procedure as in Example 2 is followed, except that the nitrocellulose membrane is incubated overnight with serum pooled from several latex-allergic patients (diluted 1:5.25 in PBS-milk and 0.05% sodium azide) as the primary antibody. Anti-human IgE conjugated to alkaline phosphatase served as the secondary antibody. The binding of human IgE to ALP on a Western blot of the protein after separation of the protein by SDS-polyacrylamide gel electrophoresis is shown in FIG. 4 (lane 3).

EXAMPLE 6

Preparation and Cloning of the cDNA Encoding ALP

The complementary DNA (cDNA) encoding the amino acid sequence of ALP can be cloned and multiplied in a host such as a micro-organism. The micro-organism can be selected from the group consisting of bacteria, yeast, and viruses. Higher plant cells can also be used as vectors. The ALP protein, in recombinant form, can then be synthesised in the same host or in an alternative host. The following is a description of the method used to clone the cDNA of ALP. Standard methods are used in the preparation and purification of DNA, mini- and maxipreps, DNA purification, restriction endonuclease digestions, agarose gel electrophoresis, ligations, transformations and poly(A)$^+$ mRNA isolation by oligo (dT) cellulose column chromatography.

Preparation of Latex mRNA

Latex is collected by tapping the *Hevea brasiliensis* tree. Before the tree is tapped, it is fitted with a sterilised drainage spout. Immediately upon tapping, the incision and spout are washed with about 20 ml of 2×RNA extraction buffer (0.1 mol Tris-HCl, 0.3 mol LiCl, 0.01 mol EDTA, 10% SDS, pH 9.5). The latex is then washed down with 100 ml of RNA extraction buffer to a total collected volume of 200 ml in a sterile conical flask. In the laboratory, the latex is mixed well and centrifuged in polyallomer tubes at 112,700 g for 30 minutes at 15° C. The aqueous phase is gently decanted into sterile centrifuge tubes and subsequent processing of the aqueous phase to isolate total RNA is performed according to the method of Prescott and Martin (1987) *Plant Mol Biol Rep*.

Synthesis of ALP cDNA

First strand cDNA synthesis is prepared by reverse transcribing 1 microgram of total latex RNA in 20 μl volume using the GeneRacer™ Kit (Invitrogen, USA) as per the vendor's instructions. Synthesis of cDNA is accomplished by PCR amplification.

The cDNA is amplified by PCR without prior purification. Each reaction is performed in a 50 μl volume containing 2 μl of the first strand reaction above, 12.5 μM of GeneRacer™ 3' Primer (5'-GCTGTCAACGATACGCTACGTAACG-3' where A,G,C and T are the abbreviations for the nucleotides bases adenine, guanine, cytosine and thymine respectively), 12.5 μM of specific primer, 0.2 mMol DATP, 0.2 mMol dTTP, 0.2 mMol dCTP, 0.2 mMol dGTP, pH 7.5, 1 unit of Taq High Fidelity (Roche Diagnostics GmbH), 10 mM Tris-Hcl, 1.5 mM MgCl$_2$, 50 mM KCl, pH 8.3, and overlayed with 50 μl of mineral oil. The PCR reaction took place in a thermocycler following the manufacturer's instructions. A second round of PCR is performed as previously but using 5 μl of the first round PCR as the template. 20 μl of the PCR amplification product is used for analysis on a 1.0% agarose gel stained with ethidium bromide.

Cloning of ALP cDNA.

The PCR product (about 1.5 Kb, in size) is ligated into the TOPO® vector (Invitrogen, USA) as per the vendor's instructions. The ligate (2 μl) is used for the transformation of One Shot® TOP10 Chemically Competent *Escherichia coli* (Invitrogen, USA) to ampicillin resistance. After incubating overnight at 37° C. in agar medium containing ampicillin (100 μg/ml), transformants were picked by Xgal (80 μg/ml)/IPTG (3 mmol/L) colour selection. The picked clones are screened by miniprep assay using the Wizard® SV Minipreps DNA Purification System (Promega, USA) as per the vendor's instructions. 1 μg of the selected clones are then sent for nucleic acid sequencing.

The DNA sequences (1394 basepairs, FIG. 1) are translated into the amino acids that they encoded (FIG. 2). The amino acid sequence encompassed the following segments:
1) ctaccaactactattatacctgctcatggtggatttagt (at position 384 to 422) (SEQ ID NO:2) encodes the peptide LPTTTIPAHGGFS (SEQ ID NO:6)
2) taccttgatgtccaatattcgcaattccgg (at position 429 to 458) (SEQ ID NO:3) encodes the peptide YLDVQYSQFR (SEQ ID NO:7)
3) tattctttattcagtgagccagaaaaa (at position 897 to 923) (SEQ ID NO:4) encodes the peptide YSLFSEPEK (SEQ ID NO:8) where a,g,c and t are the abbreviations for the nucleotides bases adenine, guanine, cytosine and thymine respectively. As noted earlier, these three protein domains had been independently identified by mass spectrometry. The applicants note that minor variations of the DNA sequence would not alter substantially the basic characteristics of the peptide that the DNA encodes.

EXAMPLE 7

Over-Expression of Recombinant ALP

There are several commercial kits that can be used for the over-expression of the allergenic latex protein. In this example, the pMAL-c2 protein fusion and purification system (New England Biolabs, USA) is used to overexpress recombinant protein from its cloned cDNA. The procedures used for the induction of fusion protein overproduction, affinity chromatography purification, cleavage of fusion protein by factor Xa protease, and purification of the target protein by hydroxyapatite chromatography are according to the vendor's instructions. In this example, isopropyl thiogalactoside (IPTG) is used as an inducer for the expression system.

Figure 6:
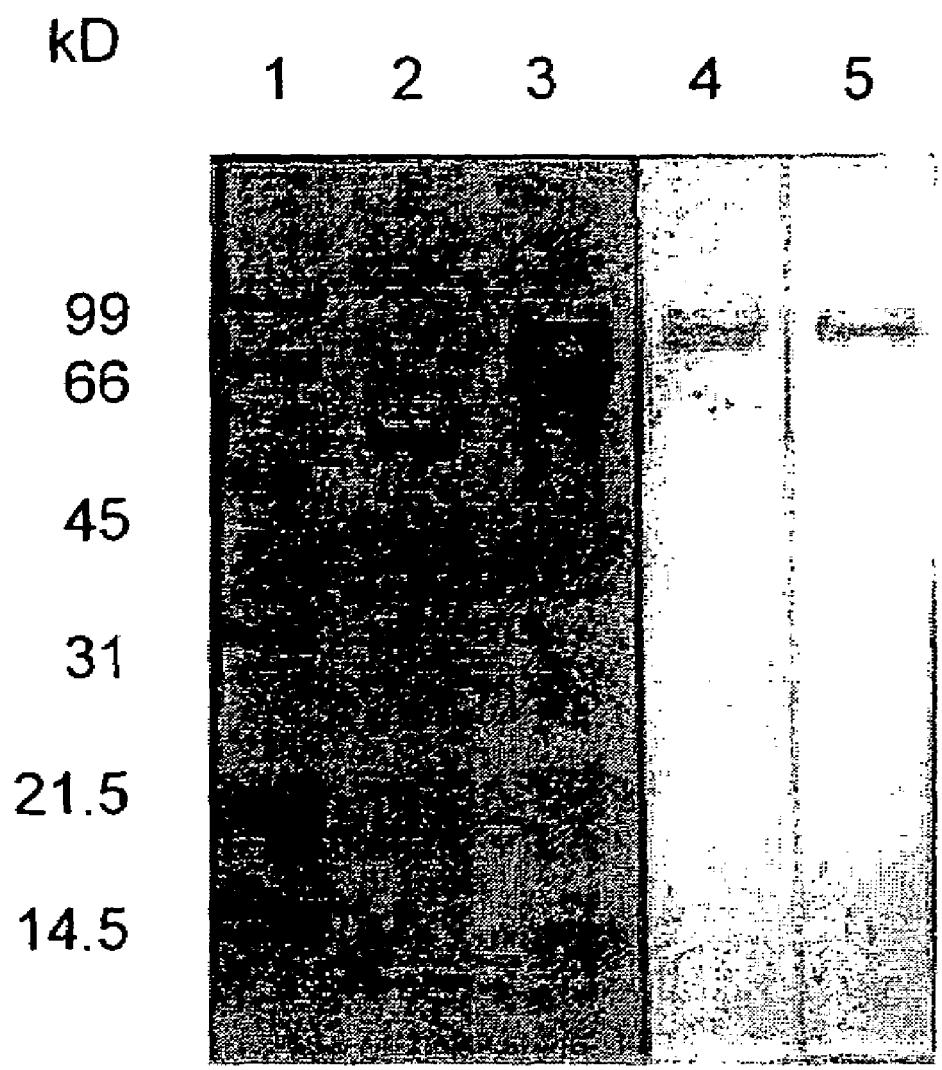
FIG. 6 shows a Western blot of the recombinant MBP-ALP fusion protein after separation by SDS-PAGE. The protein is stained with Coomassie Blue to show the electrophoretic migration of the recombinant ALP fusion protein (lane 3). Binding of recombinant ALP to monoclonal (Lane 4) and polyclonal antibodies (lane 5) developed against native ALP is also shown.

The ALP cDNA is subcloned into the vector pMAL-c2 in the same translational reading frame as the malE gene of the vector. The bacterial cells are grown overnight at 37° C. on an LB indicator plate containing 100 μg/ml ampicillin, 10 μmol isopropyl thiogalactoside (IPTG) and 10 μg/ml Xgal. White colonies are picked and screened for the presence of the MBP fusion plasmid by miniprep assay. A positive clone is then taken for the overproduction of the REF protein. IPTG-induced *E. coli* cells are disrupted by a freeze (−20° C.)/thaw cycle (ambient temperature) and sonicating (Vibra Cell, Sonics & Materials Inc., USA) in ice-water bath with 15 seconds pulses for 3 minutes. The release of fusion protein eluted from the amylose column is monitored by assaying for protein. Whereas the amino acid sequence of the peptide is determined by the cDNA sequence in the expression vector, the applicants note that minor changes in the cDNA sequence would not alter substantially the basic characteristics of the recombinant protein. FIG. 6 shows the expressed recombinant protein and its binding to antibodies that had been developed against its native (natural) counterpart purified from natural rubber latex.

EXAMPLE 8

Use of ALP in Immunoassays

Native or recombinant ALP or its molecular variant (a protein similar to ALP, but differing slightly, for example, in a few amino acids) can be used on its own, or in combination with an antibody developed against ALP or its molecular variant, in immunoassays. Molecular variants of ALP may occur naturally in latex or may exist as a result of laboratory manipulation. Such variants of ALP may differ only slightly from one another (e.g. by a few amino acids) and they have substantially similar basic functions or characteristics including allergenicity. Such immunoassays can be constructed in many different formats, but they basically rely on the immunological reaction between an antibody and its antigen. The antibody in this instance can be an antibody against ALP or its molecular variant, or human IgE. Its antigen can be native or recombinant ALP or its molecular variant, or a peptide that embodies the epitope site of ALP or its molecular variant.

The immunoassay can be used for the diagnosis of for the diagnosis of allergy to ALP or allergy to latex in general. In a different format, the immunoassay can be used for the detection of ALP in latex or latex products.

EXAMPLE 9

Use of ALP in Immunotherapy

Immunotherapy is a preventive treatment for allergic reactions that is carried out by giving gradually increasing doses of the allergen to which the person is allergic. The incremental increases of the allergen cause the immune system to become less sensitive to the substance when the substance is encountered in the future. There are several treatment protocols for immunotherapy. As an example, immunotherapy with ALP can be carried out by injecting a purified sample of ALP into the skin of the arm. An injection may be given once a week for about 30 weeks, after which injections can be administered every two weeks. Eventually, injections can be given every four weeks. The duration of therapy may be three or four years, sometimes longer. In place of native ALP, immunotherapy may also be carried out with a suitable recombinant ALP or the molecular variant of ALP (a protein similar to ALP, but differing slightly, for example, in a few amino acids), or a peptide representing a portion of ALP or its molecular variant.

From the above description, one skilled in the art can easily ascertain the essential characteristics of the present invention, and without departing from the spirit and scope thereof, can make various changes and modifications of the invention to adapt it to various usage and conditions.

The invention claimed is:

1. An isolated nucleic acid molecule comprising a nucleotide sequence encoding the amino acid sequence as set forth in SEQ ID NO:5 or conservative substitutions thereof, wherein a glycoprotein expressed from said nucleic acid molecule is capable of inducing an allergic reaction to latex in a person sensitized to said glycoprotein.

2. The nucleic acid molecule of claim 1, comprising the nucleotide sequence of SEQ ID NO:1.

3. A vector comprising the nucleic acid molecule of claim 1 or claim 2.

4. The vector of claim 3, wherein said vector is an expression vector.

5. An isolated host cell transfected with the vector of claim 4.

6. A method of expressing a glycoprotein comprising the step of culturing the isolated host cell of claim 5 under conditions in which said nucleic acid molecule is expressed, thereby expressing said glycoprotein.

7. A method for producing a glycoprotein in recombinant form, said method comprising the steps of:

(a) inserting the vector of claim 4 into an appropriate host cell; and (b) inducing the host cell to express said recombinant protein.

8. The method of claim 7, wherein the host cell is a microorganism, a plant or an animal.

9. The method of claim 8, wherein the microorganism is a yeast.

10. The method of claim 7, wherein, in step (b), said host cell is exposed to an inducer.

11. The method of claim 10, wherein said inducer is isopropyl thiogalactoside (IPTG).

* * * * *

UNITED STATES PATENT AND TRADEMARK OFFICE
CERTIFICATE OF CORRECTION

PATENT NO. : 7,329,512 B2
APPLICATION NO. : 10/789312
DATED : February 12, 2008
INVENTOR(S) : Siti Arija Mad Arif et al.

It is certified that error appears in the above-identified patent and that said Letters Patent is hereby corrected as shown below:

Column 7, line 19, "DATP" should read --dATP--;

Column 7, line 47, "LPTTTIPAHG-" should read --LPTTIIPAHG- --;

Column 15, claim 1, lines 4-5 "NO:5 or conservative substitutions thereof, wherein a glycoprotein expressed" should read --NO:5, wherein a protein expressed--;

Column 15, claim 1, line 7, "glycoprotein" should read --protein--;

Column 15, claim 6, line 16, "glycoprotein" should read --protein--;

Column 15, claim 6, line 19, "glycoprotein" should read --protein--; and

Column 16, claim 7, line 1, "glycoprotein" should read --protein--.

Signed and Sealed this

Thirtieth Day of December, 2008

JON W. DUDAS
*Director of the United States Patent and Trademark Office*

SEQUENCE LISTING

<160> NUMBER OF SEQ ID NOS: 8

<210> SEQ ID NO 1
<211> LENGTH: 1394
<212> TYPE: DNA
<213> ORGANISM: Hevea brasiliensis

<400> SEQUENCE: 1

```
acgcggggc gttaacactt ggttttgct tccacttcat ggagttccct gaaaccaata      60
acaaccctat catcactctc tctttcttat tatgcatgct ttccctagct tatgcttccg     120
aaacctgtga ttttccagca atctttaact tcggcgactc caattccgat accggtggca    180
aggcagctgc ctttatcct cttaaccctc cttatggaga gactttcttt cacaggtcga    240
caggaaggta ctctgatgga aggctcataa tagattttat cgccgagagt ttcaatctcc   300
catatctgag tccatatctt agttccctgg gaagcaactt caaacatggt gcagattttg   360
ccacagcagg atccaccatt aaactaccaa ctactattat acctgctcat ggtggattta    420
gtccattcta ccttgatgtc caatattcgc aattccggca attcataccc agatcacagt    480
ttatcaggga aactggaggc atatttgctg aattggtgcc cgaggaatat tattttgaga   540
aagctttata cacattcgat attggtcaaa atgatcttac agaaggattc ttgaacttaa    600
ctgtggaaga agtgaatgca actgtccctg atcttgtgaa tagcttctca gcaaacgtta   660
agaaaatata cgatttggga gctagaacat tttggattca caacacagga ccaattggtt   720
gtctttcatt cattttaacg tattttccct gggcagaaaa ggatagtgca ggctgtgcaa   780
aagcttacaa tgaagttgct cagcatttta atcacaagtt gaaggagatc gttgctcaac   840
tcaggaagga tttgccttta gctacattcg tccacgttga catctattct gtcaagtatt   900
ctttattcag tgagccagaa aaacacggtt tcgagtttcc acttataaca tgttgtggct   960
acggaggaaa gtacaatttt agtgttactg ctccatgtgg agatacagtt acagcagacg   1020
acggtaccaa aatagttgtg ggttcatgtg cttgcccttc agttcgagta aattgggatg   1080
gagctcacta cactgaagct gccaatgaat attttttcga ccagatttct acaggagcct   1140
tctctgatcc ccctgttcca ttgaatatgg catgtcataa aactgaatca ttgaggacat   1200
tagcctctgt ataggttata tgaaagtgct ttgctgaaag cccgctaata aaatgaggaa   1260
taataataaa tgagaaacca ttgattatgt taggattcac ttggtttcta tcataataat   1320
ctatctgttg tatatacaac agttgtatga aatagtttct tgtaataaag acttgtcttt   1380
ctccggtttc ccta                                                     1394
```

<210> SEQ ID NO 2
<211> LENGTH: 39
<212> TYPE: DNA
<213> ORGANISM: Hevea brasiliensis

<400> SEQUENCE: 2

-continued

```
ctaccaacta ctattatacc tgctcatggt ggatttagt                            39

<210> SEQ ID NO 3
<211> LENGTH: 30
<212> TYPE: DNA
<213> ORGANISM: Hevea brasiliensis

<400> SEQUENCE: 3
taccttgatg tccaatattc gcaattccgg                                      30

<210> SEQ ID NO 4
<211> LENGTH: 27
<212> TYPE: DNA
<213> ORGANISM: Hevea brasiliensis

<400> SEQUENCE: 4
tattctttat tcagtgagcc agaaaaa                                         27

<210> SEQ ID NO 5
<211> LENGTH: 464
<212> TYPE: PRT
<213> ORGANISM: Hevea brasiliensis
<220> FEATURE:
<221> NAME/KEY: VARIANT
<222> LOCATION: (1)...(464)
<223> OTHER INFORMATION: Xaa = Any Amino Acid

<400> SEQUENCE: 5
```

Ala Gly Ala Leu Thr Leu Gly Phe Cys Phe His Phe Met Glu Phe Pro
 1               5                  10                  15

Glu Thr Asn Asn Asn Pro Ile Ile Thr Leu Ser Phe Leu Leu Cys Met
            20                  25                  30

Leu Ser Leu Ala Tyr Ala Ser Glu Thr Cys Asp Phe Pro Ala Ile Phe
        35                  40                  45

Asn Phe Gly Asp Ser Asn Ser Asp Thr Gly Gly Lys Ala Ala Ala Phe
    50                  55                  60

Tyr Pro Leu Asn Pro Pro Tyr Gly Glu Thr Phe Phe His Arg Ser Thr
65                  70                  75                  80

Gly Arg Tyr Ser Asp Gly Arg Leu Ile Ile Asp Phe Ile Ala Glu Ser
                85                  90                  95

Phe Asn Leu Pro Tyr Leu Ser Pro Tyr Leu Ser Ser Leu Gly Ser Asn
            100                 105                 110

Phe Lys His Gly Ala Asp Phe Ala Thr Ala Gly Ser Thr Ile Lys Leu
        115                 120                 125

Pro Thr Thr Ile Ile Pro Ala His Gly Gly Phe Ser Pro Phe Tyr Leu
    130                 135                 140

Asp Val Gln Tyr Ser Gln Phe Arg Gln Phe Ile Pro Arg Ser Gln Phe
145                 150                 155                 160

Ile Arg Glu Thr Gly Gly Ile Phe Ala Glu Leu Val Pro Glu Glu Tyr
                165                 170                 175

Tyr Phe Glu Lys Ala Leu Tyr Thr Phe Asp Ile Gly Gln Asn Asp Leu
            180                 185                 190

Thr Glu Gly Phe Leu Asn Leu Thr Val Glu Glu Val Asn Ala Thr Val
        195                 200                 205

Pro Asp Leu Val Asn Ser Phe Ser Ala Asn Val Lys Lys Ile Tyr Asp
    210                 215                 220

```
Leu Gly Ala Arg Thr Phe Trp Ile His Asn Thr Gly Pro Ile Gly Cys
225                 230                 235                 240

Leu Ser Phe Ile Leu Thr Tyr Phe Pro Trp Ala Glu Lys Asp Ser Ala
            245                 250                 255

Gly Cys Ala Lys Ala Tyr Asn Glu Val Ala Gln His Phe Asn His Lys
            260                 265                 270

Leu Lys Glu Ile Val Ala Gln Leu Arg Lys Asp Leu Pro Leu Ala Thr
        275                 280                 285

Phe Val His Val Asp Ile Tyr Ser Val Lys Tyr Ser Leu Phe Ser Glu
    290                 295                 300

Pro Glu Lys His Gly Phe Glu Phe Pro Leu Ile Thr Cys Cys Gly Tyr
305                 310                 315                 320

Gly Gly Lys Tyr Asn Phe Ser Val Thr Ala Pro Cys Gly Asp Thr Val
            325                 330                 335

Thr Ala Asp Asp Gly Thr Lys Ile Val Val Gly Ser Cys Ala Cys Pro
            340                 345                 350

Ser Val Arg Val Asn Trp Asp Gly Ala His Tyr Thr Glu Ala Ala Asn
        355                 360                 365

Glu Tyr Phe Phe Asp Gln Ile Ser Thr Gly Ala Phe Ser Asp Pro Pro
    370                 375                 380

Val Pro Leu Asn Met Ala Cys His Lys Thr Glu Ser Leu Arg Thr Leu
385                 390                 395                 400

Ala Ser Val Xaa Val Ile Xaa Lys Cys Phe Ala Glu Ser Pro Leu Ile
            405                 410                 415

Lys Xaa Gly Ile Ile Ile Asn Glu Lys Pro Leu Ile Met Leu Gly Phe
            420                 425                 430

Thr Trp Phe Leu Ser Xaa Xaa Ser Ile Cys Cys Ile Tyr Asn Ser Cys
            435                 440                 445

Met Lys Xaa Phe Leu Val Ile Lys Thr Cys Leu Ser Pro Val Ser Leu
    450                 455                 460
```

<210> SEQ ID NO 6
<211> LENGTH: 13
<212> TYPE: PRT
<213> ORGANISM: Hevea brasiliensis

<400> SEQUENCE: 6

```
Leu Pro Thr Thr Ile Ile Pro Ala His Gly Gly Phe Ser
1               5                   10
```

<210> SEQ ID NO 7
<211> LENGTH: 10
<212> TYPE: PRT
<213> ORGANISM: Hevea brasiliensis

<400> SEQUENCE: 7

```
Tyr Leu Asp Val Gln Tyr Ser Gln Phe Arg
1               5                   10
```

<210> SEQ ID NO 8
<211> LENGTH: 9
<212> TYPE: PRT
<213> ORGANISM: Hevea brasiliensis

<400> SEQUENCE: 8

```
Tyr Ser Leu Phe Ser Glu Pro Glu Lys
1               5
```